United States Patent
Sandhu et al.

(10) Patent No.: US 9,517,160 B2
(45) Date of Patent: *Dec. 13, 2016

(54) COOLING ELEMENTS WITH BANDS

(71) Applicant: Cryothermic Systems, Inc., Broadview Heights, OH (US)

(72) Inventors: Aqeel A. Sandhu, North Canton, OH (US); Scott Raybuck, Hinckley, OH (US); Brian J. Seitz, Broadview Heights, OH (US)

(73) Assignee: CRYOTHERMIC SYSTEMS, INC., Broadview Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/951,758

(22) Filed: Nov. 25, 2015

(65) Prior Publication Data

US 2016/0081848 A1 Mar. 24, 2016

Related U.S. Application Data

(63) Continuation of application No. 13/616,705, filed on Sep. 14, 2012, now Pat. No. 9,226,847, which is a
(Continued)

(51) Int. Cl.
*A61F 5/00* (2006.01)
*A61F 7/10* (2006.01)
(Continued)

(52) U.S. Cl.
CPC ............... *A61F 7/106* (2013.01); *A61F 5/055* (2013.01); *A61F 2007/001* (2013.01); *A61F 2007/0012* (2013.01); *A61F 2007/0276* (2013.01)

(58) Field of Classification Search
CPC .... A61F 2007/0009; A61F 5/055; A61F 7/00; A61F 7/02; A61F 2007/0056; A61F 2007/0012; A61F 2007/0054; A61F 2007/0095; A61F 2007/0225; A61F 2007/0276; A61F 7/106; A61F 2007/0002; A61F 2007/001; A61F 2007/0018; A61F 2007/0042; A61F 7/10; A61F 2007/0008; A61F 2007/023
(Continued)

(56) References Cited

U.S. PATENT DOCUMENTS 2,801,630 A 8/1957 Moore
2,911,970 A 11/1959 Bartels
(Continued)

FOREIGN PATENT DOCUMENTS

WO 0007529 A1 2/2000

OTHER PUBLICATIONS

"Material Safety Data Sheets", Sep. 6, 2005, pp. 1-16; Available at: http://www.sportshealth.com/media/pdf/msds/InstaKool%2037139.pdf.
(Continued)

*Primary Examiner* — Michael Brown
(74) *Attorney, Agent, or Firm* — Benesch, Friedlander, Coplan & Aronoff LLP (57) ABSTRACT

A kit for cooling the blood in the carotid arteries includes a cervical immobilization collar and a cooling element. The cooling element may include a body-facing panel attached on a body-facing surface to a lining layer, an outward-facing panel, and cooling material disposed between the body-facing panel and the outward facing panel. The cooling material may comprise urea and Carbamakool™ in an amount sufficient to produce a temperature of 20° F. to 35° F. within a minute of activation when measured on the body-facing surface of the body-facing panel.

16 Claims, 7 Drawing Sheets

Related U.S. Application Data continuation-in-part of application No. 12/913,412, filed on Oct. 27, 2010, now Pat. No. 8,267,878, which is a continuation-in-part of application No. 12/429,663, filed on Apr. 24, 2009, now Pat. No. 7,846,118, which is a continuation-in-part of application No. 11/162,922, filed on Sep. 28, 2005, now abandoned.

(51) Int. Cl.
*A61F 5/055* (2006.01)
*A61F 7/00* (2006.01)
*A61F 7/02* (2006.01)

(58) Field of Classification Search
USPC .............................. 602/17–18; 128/DIG. 23
See application file for complete search history.

(56) References Cited

U.S. PATENT DOCUMENTS

| | | | |
|---|---|---|---|
| 3,042,026 A | 7/1962 | Monfardini | |
| D202,868 S | 11/1965 | Marks | |
| D203,018 S | 11/1965 | Helferich | |
| D213,742 S | 4/1969 | Bond | |
| 4,057,047 A | 11/1977 | Gossett | |
| 4,137,769 A | 2/1979 | Parker | |
| 4,325,254 A | 4/1982 | Svacina et al. | |
| 4,427,010 A | 1/1984 | Marx | |
| 4,745,922 A | 5/1988 | Taylor | |
| 4,783,866 A | 11/1988 | Simmons et al. | |
| 4,827,915 A | 5/1989 | Gorsen | |
| 4,832,030 A | 5/1989 | De Canto | |
| 5,005,374 A | 4/1991 | Spitler | |
| 5,007,416 A | 4/1991 | Burns et al. | |
| 5,010,877 A | 4/1991 | Druskoczi | |
| 5,184,613 A | 2/1993 | Mintz | |
| 5,300,105 A | 4/1994 | Owens | |
| 1,525,771 A | 2/1995 | Falconer | |
| 5,415,624 A | 5/1995 | Williams | |
| RE35,290 E | 7/1996 | Druskoczi | |
| 5,575,812 A | 11/1996 | Owens | |
| 5,622,529 A | 4/1997 | Calabrese | |
| 5,626,151 A | 5/1997 | Linden | |
| 5,752,926 A | 5/1998 | Larson et al. | |
| 5,795,315 A | 8/1998 | Traut et al. | |
| 5,797,713 A | 8/1998 | Tweardy et al. | |
| 5,916,242 A | 6/1999 | Schwartz | |
| 6,030,412 A | 2/2000 | Klatz et al. | |
| 6,126,680 A | 10/2000 | Wass | |
| 6,231,535 B1 | 5/2001 | Mainiero et al. | |
| 6,416,532 B1 | 7/2002 | Fallik | |
| 6,494,854 B1 | 12/2002 | Visness et al. | |
| 6,497,721 B2 | 12/2002 | Ginsburg et al. | |
| 6,508,831 B1 | 1/2003 | Kushnir | |
| 6,527,798 B2 | 3/2003 | Ginsburg et al. | |
| 6,599,312 B2 * | 7/2003 | Dobak, III | A61F 7/12 607/105 |
| 6,620,188 B1 | 9/2003 | Ginsburg et al. | |
| 6,682,552 B2 | 1/2004 | Ramsden et al. | |
| 6,865,825 B2 | 3/2005 | Bailey, Sr. et al. | |
| 7,090,652 B2 | 8/2006 | Santelli, Jr. | |
| 7,361,186 B2 | 4/2008 | Voorhees et al. | |
| D616,997 S | 6/2010 | Thorgilsdottir et al. | |
| 7,846,118 B2 | 12/2010 | Sandhu | |
| 8,267,878 B2 * | 9/2012 | Sandhu | A61F 5/055 128/DIG. 23 |
| 9,089,411 B2 * | 7/2015 | Sandhu | A61F 5/055 |
| 9,226,847 B2 * | 1/2016 | Sandhu | A61F 7/106 |
| 2002/0103520 A1 * | 8/2002 | Latham | A61F 7/10 607/108 |
| 2003/0055473 A1 | 3/2003 | Ramsden et al. | |
| 2009/0209893 A1 * | 8/2009 | Sandhu | A61F 5/055 602/18 |

OTHER PUBLICATIONS

"CFR—Code of Federal Regulations Title 21, vol. 8, revised as of Apr. 1, 2013" Food and Drugs, Chapter I—Food and Drug Administration Department of Health and Human Services—Subchapter H—Medical Devices.

"Pre-Hospital Cervical Spinal Immobilization of Following Trauma", the Section on Disorders of the Spine and Peripheral Nerves of the American Association of Neurological Surgeons and the Congress of Neurological Surgeons. Sep. 20, 2001.

International Search Report and Written Opinion for PCT/US2013/058457, mailed Dec. 16, 2013.

International Search Report and Written Opinion for PCT/US2011-058090, mailed May 4, 2012.

International Search Report for PCT/US2005/035095, mailed Jun. 30, 2006.

* cited by examiner

COOLING ELEMENTS WITH BANDS

CROSS-REFERENCE TO RELATED APPLICATIONS

This application is a continuation of U.S. patent application Ser. No. 13/616,705, filed on Sep. 14, 2012, which is a continuation-in-part of U.S. patent application Ser. No. 12/913,412, filed Oct. 27, 2010 now issued as U.S. Pat. No. 8,267,878, which is a continuation-in-part of U.S. patent application Ser. No. 12/429,663, filed Apr. 24, 2009 now issued as U.S. Pat. No. 7,846,118, which is a continuation of U.S. patent application Ser. No. 11/162,922, filed Sep. 28, 2005, now abandoned, all of which are incorporated by reference herein.

BACKGROUND

Embodiments of the present disclosure can relate to cervical immobilization and to therapeutic induction of mild cerebral hypothermia by transcutaneous cooling of oxygenated blood flowing through carotid arteries.

Cervical immobilization collars are often used by first-responders, such as EMTs, to stabilize the neck, head, and spine of a patient immediately after a trauma has occurred. While this procedure is generally effective to prevent further injury, it is helpful to begin to treat the patient's trauma before reaching the hospital. One method of treatment may include cooling the patient's brain. Brain cooling, i.e., reducing brain temperatures by as little as one or two degrees Celsius, produces a neuroprotective effect against deleterious responses associated with brain injuries. This mild cerebral hypothermia inhibits the release of neuroexcitetory amino acids (e.g., aspartate and glutamine), thereby interrupting the cascading effects of the inflammatory response. The neuroprotective effect is most pronounced if brain cooling is affected as soon as possible following an injury.

Protocols for first responders generally do not incorporate effective procedures for initiating brain cooling. For example, it is known to apply cold packs to the patient's body, to the groin, skull, and under the arm. This type of cooling, however, imparts systemic cooling, rather than selective cooling, and may not effectively drop the temperature of the patient's brain.

SUMMARY

A kit for cooling the blood in the carotid arteries includes a cooling element and a cervical immobilization collar. The cooling element includes a body-facing panel, an outward-facing panel, and a cooling material disposed between the body-facing panel and the outward facing panel. The cooling material may be comprised of urea and Carbamakool. The cooling material is capable of producing a temperature of 20° F. to 35° F. within a minute of activation when measured on the body-facing surface of the body-facing panel and may be capable of maintaining the temperature for a period of about 15 to about 30 minutes. The cervical immobilization collar may include a substantially annular support structure with an extended axial length and an anterior opening.

In another embodiment, cooling element can include a body-facing panel, an outward facing panel, cooling material, and a band. The body-facing panel can be attached on a body-facing surface. The body-facing panel and the outward-facing panel can form an end. The cooling material can be disposed between the body-facing panel and the outward facing panel. The cooling material can produce a temperature of 20° F. to 35° F. within a minute of activation at ambient temperature, when measured on the body-facing surface of the body-facing panel. The cooling material can include comprise water, urea, and an endothermic ingredient. The band can be attached to the end and configured wrap around a patient.

DETAILED DESCRIPTION

A cervical immobilization collar 10 may be used to stabilize a patient's spine, neck, and head immediately following a trauma. As shown in FIGS. 1-3 and 7, a cervical immobilization collar 10 for use with cooling elements may generally include a substantially annular support structure 12 with an anterior portion 16, which wraps around the front of the patient's neck, and a posterior portion 18, which wraps around the back of the patient's neck. The anterior portion 16 and the posterior portion 18 may be formed of a single piece of material. In an alternative embodiment, the anterior portion 16 and posterior portion 18 may be separate components connected on one or both sides of the neck by a joint or by an attachment mechanism, such as a hook and loop fastener. The substantially annular support structure 12 can be formed (preferably by pour or injection molding) from a variety of materials including plastics, polymers, or carbon or poly-paraphenylene terephthalamide fiber. In one embodiment, the annular support structure 12 comprises SCLAIR®2712 high density polyethylene, manufactured by NOVA Chemicals supplied by Entec Polymers.

Figure 2:
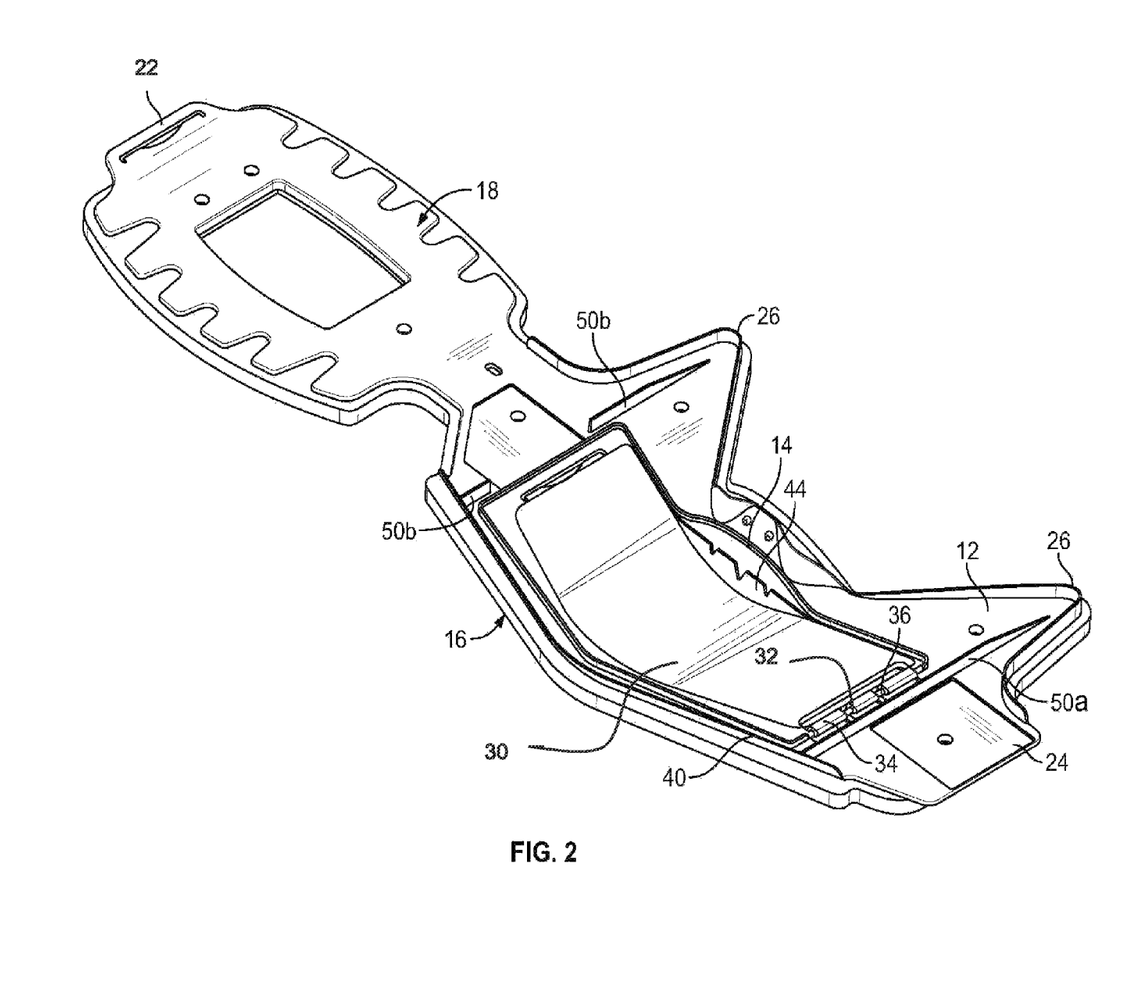
FIG. 2 is a top view of a the cervical immobilization collar.
Figure 3:
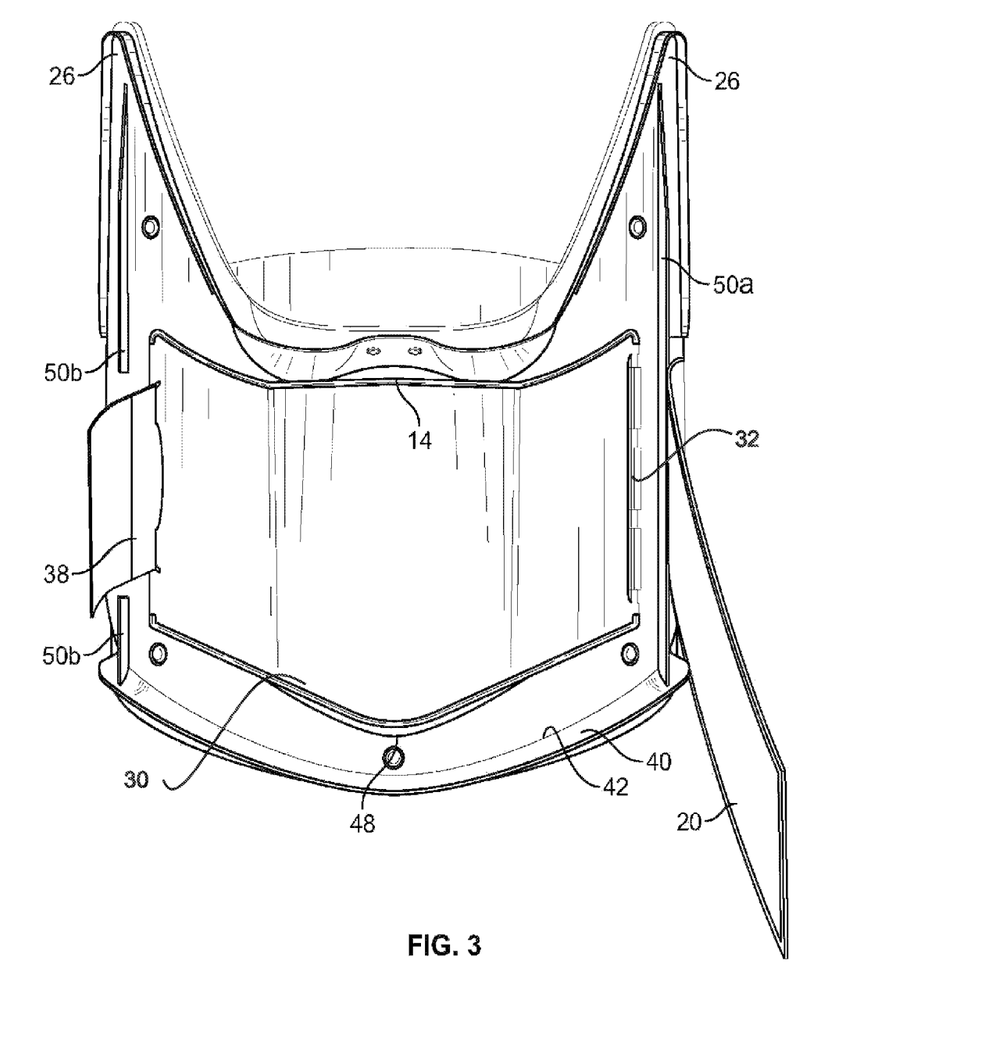
FIG. 3 is a front view of the cervical immobilization collar.

Referring to FIGS. 2 and 3, a hook and loop fastener strap 20 (as shown in FIG. 3) extends from a distal end 22 of the posterior portion 18 for releasably engaging a mating hook-and-loop fastener patch (not shown) mounted on the proximal end 24 of the anterior portion 16 of the substantially annular support structure 12.

The anterior portion 16 of the substantially annular support structure 12 may include cheek support structures 26. The cheek support structures 26 may generally extend vertically from the either side of the chin rest 14 and are configured to cover the area generally associated with the patient's cheek. The cheek support structures 26 may be used to prevent significant rotational or lateral movement of the patient's head. The cheek support structures 26 may be formed integrally as a part of the substantially annular support structure 12, as shown, or may be formed separately and mounted on to the substantially annular support structure 12 with an appropriate adhesive or attachment mechanism. In another embodiment (not shown), the annular support structure 12 may not include cheek supports.

Referring again to FIG. 1, the cervical immobilization collar 10 also includes an anterior opening 28 in the anterior portion 16 of the substantially annular support structure 12. The anterior opening 28 is defined by the frame of the substantially annular support structure 12. Traditional neck braces may include an opening in the front of the brace, but the opening is generally only large enough to provide access to the patient's trachea in a case of a blocked airway. Alternatively, the anterior opening 28 in the cervical immobilization collar 10 is designed to traverse the front of the patient's neck, exposing both of the patient's carotid artery regions, as opposed to only the trachea region.

Figure 1:
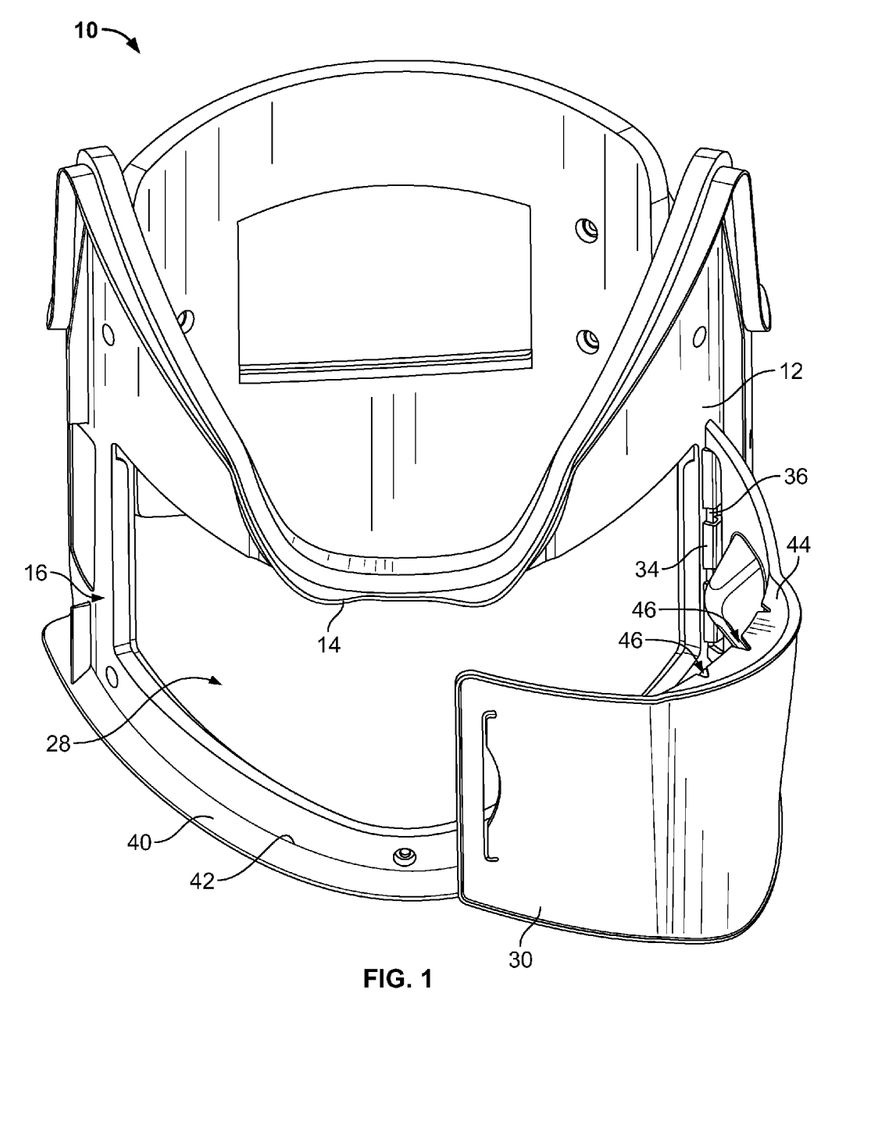
FIG. 1 is perspective view of a cervical immobilization collar.

As shown in FIG. 2, the cervical immobilization collar 10 also includes a door 30 that covers the anterior opening 28. In this embodiment, a first edge portion of the door 30 is attached to the frame of the substantially annular support structure 12 at or about one end, or a first edge portion, of the anterior opening 28 with a hinge 32, or other appropriate fastening mechanism. As shown in FIGS. 1 and 2, in one embodiment, a two part hinge may be used. In this embodiment, the first part of the hinge 34 may be integrally formed as part of the frame of the substantially annular support structure 12. Specifically, the first part of the hinge 34 may comprise from one, and preferably three, elastically deformable flanges. The second part of the hinge 36 may be integrally formed as part of the first edge portion of the door 30. The second part of the hinge 36 may snapped in to place within the first part of the hinge 34 by deforming the flanges. Once snapped in place, the second part of the hinge 36 is rotatable within the flanges of the first part of the hinge 34 so that the door 30 may be opened and closed, relative to the frame of the substantially annular support structure 12. In another embodiment, the hinge 32 may be a living hinge (not shown) that is integrally formed between the first edge portion of the door 30 and the frame of the annular support structure 12.

A second edge portion of the door 30 may be fastened to the frame of the substantially annular support structure 12 at a second edge portion of the anterior opening 28 with second hook and loop fastener strap 38 (shown in FIG. 3), which extends from the second edge portion of the door 30, and a mating hook-and-loop fastener patch (not shown) mounted on or about the frame of the substantially annular support structure 12 at or near the second edge portion of the anterior opening 28. The closure may also be effectuated with a snap fit mechanism; pressure fit mechanisms, buttons, latches, adhesives, or other appropriate fastening mechanism.

As discussed above, the anterior opening 28 extends substantially across the majority of the anterior portion 16 of the substantially annular support structure 12. The immobilization collar 10, however, must be strong enough to support the patient's neck and prevent flexion, or movement in which the chin is lowered down toward the chest. In traditional neck braces, this strength is provided by the structural material between the chin rest and the bottom of the brace. However, the large anterior opening 28, and lack of structural material between the chin rest 14 and the bottom of the collar 10, may compromise the strength and support provided by the immobilization collar 10, particularly in the vertical plane. Thus, the patient may be able to move their head up and down, even when wearing the collar 10. In order to provide the needed support and, thus, significantly hinder the patient's ability to move their head up and down, support members are built into the substantially annular support structure 12.

As shown in FIG. 1, a horizontally protruding ledge 40 may extend perpendicularly from a bottom edge 42 of the anterior portion of the annular support structure 12. In one embodiment, the ledge 40 may be integrally formed as part of the annular support structure 12 and may preferably extend across the entire anterior portion 16 of the frame of the substantially annular support structure 12. Similarly, the door 30 may include a shelf 44 that extends perpendicularly from the top edge of the door 30, as shown in FIG. 1, inward toward the patient's body. The shelf 44 may be integrally formed as part of the door 30. The shelf 44 may also include gaps 46 that allow the shelf 44, as part of the door 30, to bend during use.

When the door 30 is closed, as shown in FIG. 3, and the patient attempts to move their head down, the bottom 48 of the door 30 abuts the ledge 40. Similarly, the shelf 44 (shown in FIGS. 1 and 2) on the door 30 will abut the bottom of the chin rest 14, hindering the downward movement and effectively using the door 30 as the structural material between the chin rest 14 and the bottom of the collar 10.

Lateral ribs 50a and 50b may be included as well to add structural support to the anterior portion of the annular support structure 12. As shown in FIGS. 2 and 3, the lateral ribs 50a and 50b are integrally formed on the exterior surface of the annular support structure 12 and extend from under the apex of the cheek support structures 26 and abut the ledge 40. As shown in FIG. 3, lateral rib 50b may be formed of two separate pieces, a first extending from the apex of the cheek support 26 and a second extending up from the ledge 40, to accommodate the hook and loop fastener on the door 30.

Figure 4:
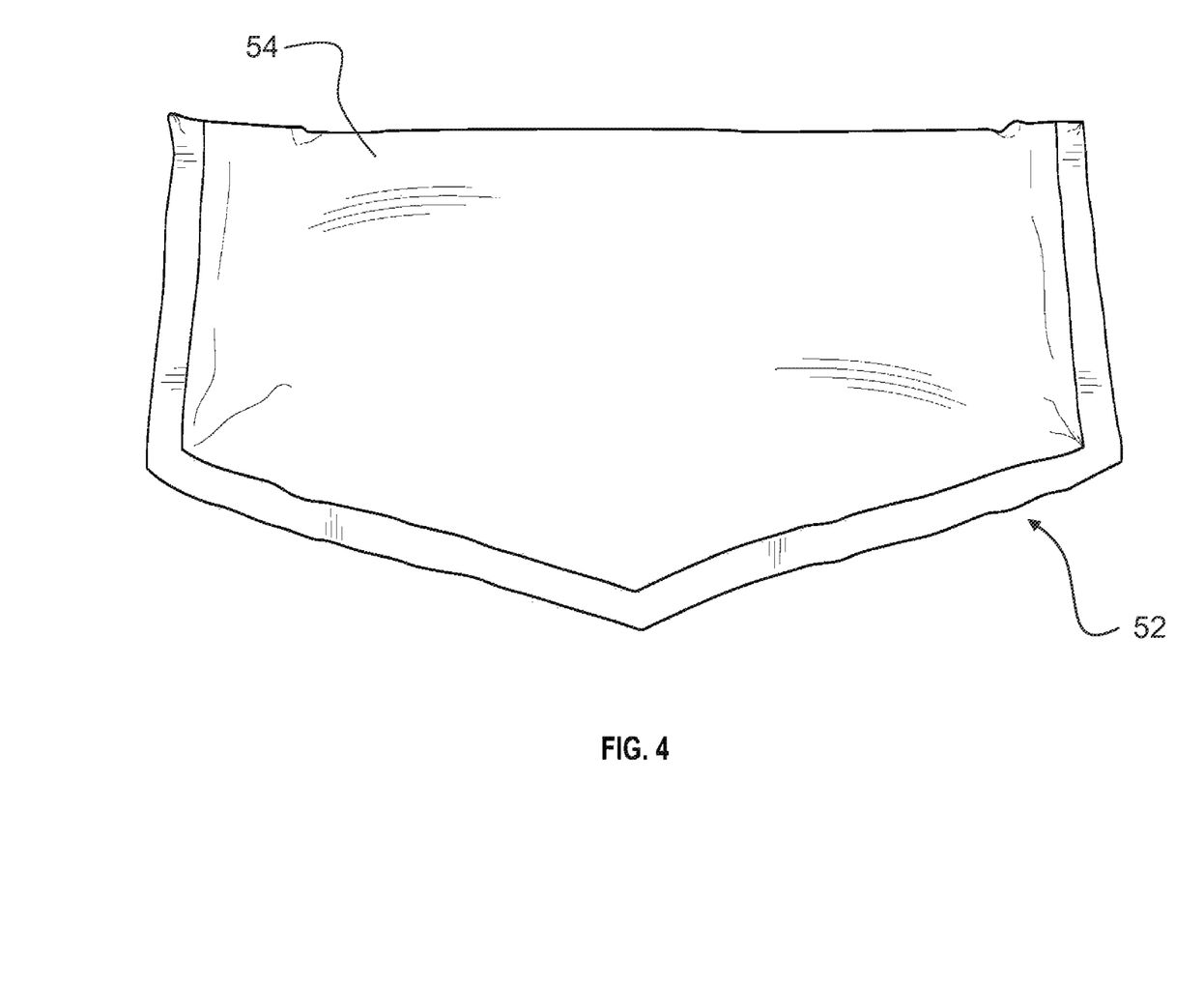
FIG. 4 is a top view of a cooling element for use in the cervical immobilization collar.

The cervical immobilization collar 10 may be used in conjunction with a cooling element 52. The cooling element 52, shown in FIG. 4, may have a shape that is substantially similar, or slightly larger, than the shape of the anterior opening 28, although the shape may take other forms, and may have a flexible, rigid, or quasi-rigid structure. The cooling element 52 may include a body-facing panel 54 and an outward-facing panel (not shown). In one embodiment, the body-facing panel 54 and the outward-facing panel may be secured at their edges with a heat-activated adhesive seal or other appropriate sealing mechanism. The cooling element 52 may be separate from or integral with the cervical immobilization collar 10.

In one embodiment, the cooling element 52 is separate from the cervical immobilization collar 10. In this embodiment, the body-facing panel 54 and the outward-facing panel may be formed of one sheet of material that is folded in half and sealed at its open edges or two sheets of material that are sealed along all of their edges. The cooling element 52 may include cooling material that produces endothermic reactions, previously chilled gels, or other materials having the capacity to absorb heat. Once the components of the endothermic packs are mixed or the element is otherwise activated, the cooling element 52 is preferably put into immediate use.

In one embodiment, the panels may include a lining layer, that covers at least the body-facing panel 54 of the cooling element 52 that comes into contact with the patient's neck. In one embodiment, the lining layer substantially covers the body-facing panel 54 of the cooling element 52. In another embodiment, both panels of the cooling element 52 are covered with the lining layer. The lining layer may be made of fabric, for example a non-woven material. It should be appreciated that the lining layer may be made of any material capable of providing comfort and preventing skin irritation, skin degradation, and potential frostbite. The lining layer may be adhered to the panels or may be detachable.

In one embodiment, the panels of the cooling element include a lining layer comprised of a non-woven material that is adhered to one or both of the panels. The panels may be comprised of a film-like material. In one example, a 0.007 mm non-woven lining layer is laminated onto a 2.5 mm linear low density white polyethylene film to form both panels of the cooling element 52. The water permeability of the panels may be 0.41 grams/100 sq in/24 hrs and the oxygen gas permeability may be less than 9.0 cc/100 sq in/24 hrs.

In this embodiment, the cooling element 52 may be approximately 10 to about 12 inches long and may include about 90 to about 110 g urea, about 45 to about 55 g Carbamakool™, and water. In another embodiment, the cooling element 52 may be about 10 inches long and include about 100 g urea, about 50 g Carbamakool™, and water. In another embodiment, the cooling element 36 may be about 11 inches long and include about 110 g urea, about 55 g Carbamakool™, and water. In these embodiments, the crystal like urea and Carbamakool™ are mixed together and sealed between the panels of the cooling element 52. In this embodiment, the cooling element 52 also includes a liquid-filled, preferably water, frangible packet (not shown). The liquid-filled packet is also sealed between the panels of the cooling element 52. To activate the cooling element 52, a user, applying pressure to the cooling element 52, ruptures the packet, which wets the urea and Carbamakool™. The user then shakes the cooling element 52 to mix the ingredients and initiate an endothermic reaction.

The cooling material in the cooling element preferably reaches a temperature of 20° F. to 45° F., desirably 25° F. to 35° F., within a minute of activation, and maintains the temperature for a period of about 10 to about 30 minutes, preferably from about 15 to about 20 minutes. Suitable cooling materials for the cooling elements 52 are available from Nortech Labs, 125 Sherwood Avenue Farmingdale N.Y. 11735.

Unlike known cold packs, which come with instructions directing the users not to place cold pack directly on the patient's skin, the cooling element 52, including a fabric lining layer laminated to the panels, allows the user to place the cooling element 52 directly on the skin of the patient for up to 20 to 30 minutes. Moreover, laminating, or otherwise adhering, the fabric lining layer to the panels film prevents the cooling element 52 from slipping out of place and away from the carotid arteries when in use against the patient's neck.

The reduced temperature produced by the mixture of urea, Carbamakool™, and water is measured on the outer surface of the cooling element 52. In other words, the temperature that the patient comes in contact with is measured to evaluate the amount of heat extraction effectuated by the cooling element 52. Using a fabric lining layer, however, insulates the cooling element 52, and therefore the internal capacity of the cooling element 52 and the amount of urea and Carbamakool™ used therein is important to properly extract heat from the patient's carotid arteries.

EXAMPLE

One lot of cooling elements 52, samples A-E, were tested. Each sample was 10 inches in length and included 100 g urea, and 50 g Carbamakool™. Both panels of samples A-E were comprised of a 0.007 mm non-woven lining layer laminated onto a 2.5 mm linear low density white polyethylene film.

The samples were activated by squeezing the samples to break a water-filled frangible packet that was sealed within the panels, then shaking each sample ten (10) times. The samples were folded and inserted into 16 oz Styrofoam cups. The ambient temperature, 68.7° F., was recorded and thermocouples were place in the fold of each cooling element about one inch from the bottom of the cups. Temperature readings were recorded once a minute with the last recording made after 30 minutes. Each cooling element was re-shaken after a two minute elapsed time. The results are shown in Table I below:

TABLE I

| Time (min) | Sample A | Sample B | Sample C | Sample D | Sample E |
| --- | --- | --- | --- | --- | --- |
| 1 | 68.7 | 68.7 | 68.7 | 68.7 | 68.7 |
| 2 | 42.0 | 27.3 | 30.0 | 30.7 | 27.3 |
| 3 | 35.0 | 24.8 | 28.5 | 27.0 | 24.6 |
| 4 | 34.9 | 24.0 | 27.1 | 35.7 | 24.1 |
| 5 | 35.1 | 23.8 | 26.9 | 25.6 | 24.3 |
| 6 | 35.3 | 23.7 | 26.9 | 25.8 | 24.5 |
| 7 | 35.5 | 23.8 | 29.9 | 25.4 | 24.7 |
| 8 | 35.7 | 24.0 | 27.2 | 25.5 | 25.2 |
| 9 | 35.9 | 24.2 | 27.3 | 26.1 | 24.1 |
| 10 | 36.1 | 24.5 | 27.9 | 25.9 | 24.4 |
| 11 | 36.2 | 24.9 | 28.1 | 25.0 | 24.9 |
| 12 | 36.4 | 25.2 | 28.5 | 26.2 | 25.0 |
| 13 | 36.6 | 25.5 | 29.9 | 26.7 | 25.3 |
| 14 | 36.8 | 25.8 | 29.4 | 27.0 | 25.9 |
| 15 | 37.0 | 26.2 | 29.7 | 27.3 | 25.0 |
| 16 | 37.1 | 26.5 | 30.0 | 27.7 | 26.3 |
| 17 | 37.3 | 26.0 | 30.5 | 28.1 | 26.5 |
| 18 | 37.5 | 27.1 | 30.8 | 28.5 | 26.8 |
| 19 | 37.7 | 27.5 | 31.3 | 28.9 | 27.1 |
| 20 | 37.9 | 27.8 | 31.6 | 29.3 | 27.2 |
| 21 | 38.1 | 28.1 | 31.9 | 29.6 | 27.5 |
| 22 | 38.3 | 28.5 | 32.3 | 30.0 | 27.9 |
| 23 | 38.6 | 28.7 | 32.7 | 30.5 | 28.4 |
| 24 | 38.8 | 29.1 | 32.9 | 30.6 | 28.7 |
| 25 | 39.0 | 29.5 | 33.3 | 30.8 | 28.9 |
| 26 | 39.2 | 29.8 | 33.5 | 31.2 | 29.1 |
| 27 | 39.4 | 30.1 | 34.1 | 31.5 | 29.5 |
| 28 | 39.5 | 30.5 | 34.4 | 31.7 | 29.8 |
| 29 | 39.8 | 30.8 | 37.7 | 32.0 | 30.0 |
| 30 | 40.0 | 31.1 | 35.1 | 32.3 | 30.1 |

Samples A-E were compared with commercially available un-lined cold packs from Medlogix Inc., P.O. Box 2157, Chester Va. 23831 (product code 10-01) (Standards A-E). The lots of un-lined commercially available code packs were comprised of urea and water. Standards A-E were activated by squeezing then shaking 10 times. The Standards were folded and inserted into 16 oz Styrofoam cups. The ambient temperature, 68.7° F., was recorded and thermocouples were place in the fold of each Standard about one inch from the bottom of the cups. Temperature readings were recorded once a minute with the last recording made after 30 minutes. Each Standard was reshaken after a two minute elapsed time. The results are shown in Table II below:

TABLE II

| Time (min) | Standard A | Standard B | Standard C | Standard D | Standard E |
| --- | --- | --- | --- | --- | --- |
| 1 | 67.8 | 67.8 | 67.8 | 67.8 | 67.8 |
| 2 | 53.3 | 54.3 | 55.9 | 50.2 | 57.5 |
| 3 | 52.9 | 53.4 | 54.5 | 49.1 | 53.2 |
| 4 | 52.3 | 44.9 | 51.3 | 48.4 | 42.4 |
| 5 | 45.1 | 44.5 | 50.7 | 52.2 | 38.1 |
| 6 | 41.7 | 44.7 | 51.2 | 52.6 | 37.7 |
| 7 | 41.2 | 45.3 | 51.1 | 52.7 | 37.7 |
| 8 | 41.5 | 45.3 | 51.3 | 52.9 | 38.0 |

TABLE II-continued

| Time (min) | Standard A | Standard B | Standard C | Standard D | Standard E |
|---|---|---|---|---|---|
| 9 | 42.5 | 45.4 | 51.7 | 52.3 | 38.2 |
| 10 | 42.5 | 45.4 | 51.1 | 52.0 | 38.5 |
| 11 | 43.3 | 45.6 | 51.3 | 52.1 | 38.8 |
| 12 | 45.2 | 45.7 | 51.5 | 52.3 | 38.9 |
| 13 | 46.1 | 45.7 | 51.6 | 51.7 | 39.2 |
| 14 | 46.5 | 45.7 | 51.6 | 51.3 | 39.5 |
| 15 | 47.0 | 46.1 | 51.6 | 51.4 | 39.9 |
| 16 | 47.8 | 46.0 | 51.6 | 51.7 | 40.1 |
| 17 | 47.8 | 46.1 | 51.5 | 51.9 | 40.3 |
| 18 | 47.7 | 46.7 | 51.0 | 51.7 | 40.3 |
| 19 | 47.1 | 46.7 | 50.3 | 51.7 | 40.5 |
| 20 | 47.3 | 46.7 | 50.9 | 51.5 | 40.9 |
| 21 | 47.3 | 46.7 | 50.4 | 51.7 | 41.1 |
| 22 | 47.2 | 46.8 | 51.3 | 51.7 | 41.3 |
| 23 | 47.5 | 47.4 | 51.3 | 51.8 | 41.4 |
| 24 | 47.6 | 47.5 | 51.8 | 52.0 | 41.7 |
| 25 | 47.7 | 47.6 | 52.0 | 52.1 | 42.4 |
| 26 | 47.9 | 47.7 | 52.1 | 52.1 | 42.3 |
| 27 | 48.1 | 47.9 | 52.1 | 52.3 | 42.3 |
| 28 | 48.1 | 48.0 | 52.3 | 52.1 | 42.9 |
| 29 | 48.4 | 48.1 | 52.3 | 52.5 | 43.1 |
| 30 | 48.6 | 48.5 | 52.4 | 51.9 | 43.3 |

The standards were compared with the cooling elements by comparing the average temperatures at each time. The results are shown in Table III, below.

TABLE III

| Time (min) | Excel Series 1 | Medlogix Series 2 |
|---|---|---|
| 1 | 68.7 | 67.8 |
| 2 | 31.46 | 54.24 |
| 3 | 27.98 | 52.62 |
| 4 | 29.16 | 47.86 |
| 5 | 27.14 | 46.12 |
| 6 | 27.24 | 45.58 |
| 7 | 27.86 | 45.6 |
| 8 | 27.52 | 45.8 |
| 9 | 27.52 | 46.02 |
| 10 | 27.76 | 45.9 |
| 11 | 27.82 | 46.22 |
| 12 | 28.26 | 46.72 |
| 13 | 28.8 | 46.86 |
| 14 | 28.98 | 46.92 |
| 15 | 29.04 | 47.2 |
| 16 | 29.52 | 47.44 |
| 17 | 29.68 | 47.52 |
| 18 | 30.14 | 47.48 |
| 19 | 30.5 | 47.26 |
| 20 | 30.76 | 47.46 |
| 11 | 31.04 | 47.44 |
| 12 | 31.4 | 47.66 |
| 13 | 31.78 | 47.88 |
| 14 | 32.02 | 48.12 |
| 15 | 32.3 | 48.36 |
| 16 | 32.56 | 48.42 |
| 17 | 32.92 | 48.54 |
| 18 | 33.18 | 48.68 |
| 19 | 34.06 | 48.88 |
| 20 | 33.72 | 48.94 |

Figure 5:
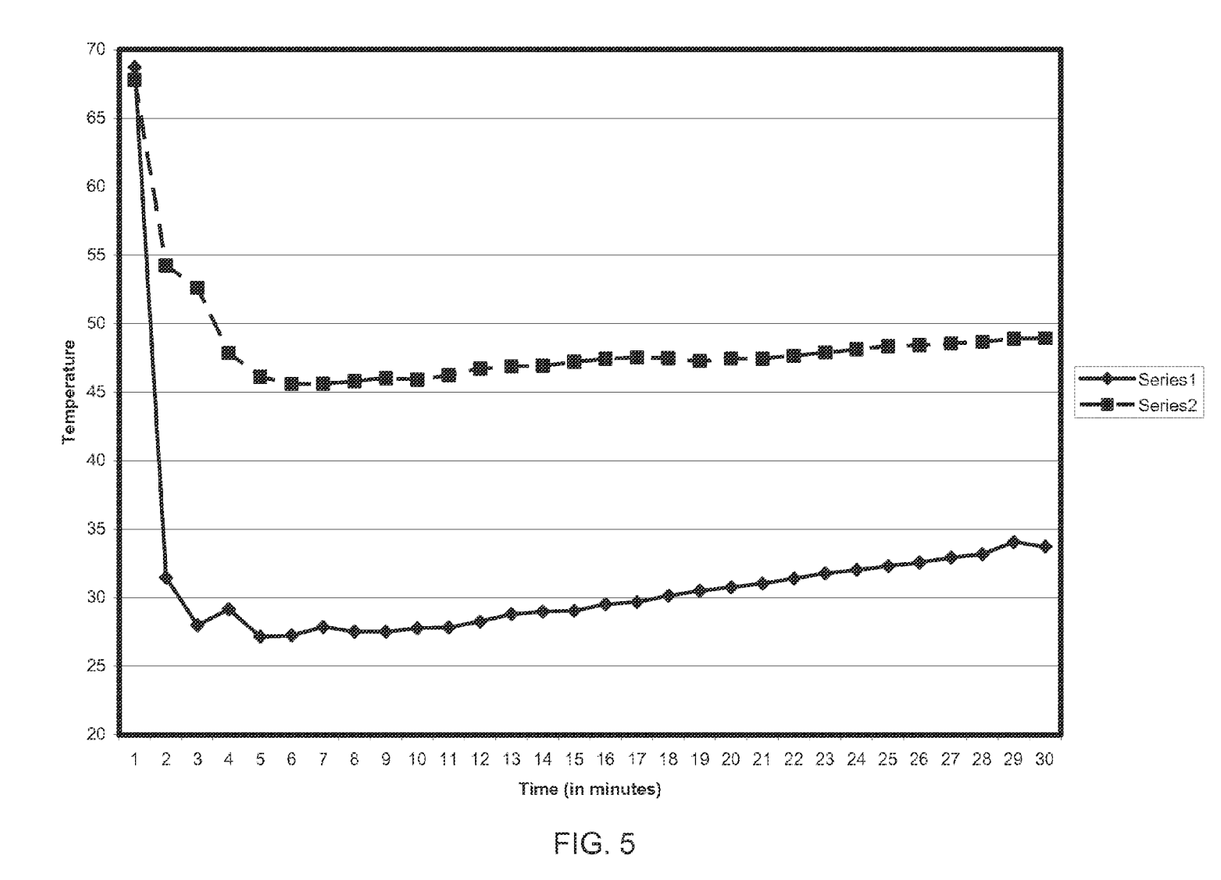
FIG. 5 is a graphical representation of the temperatures obtained by the activated cooling element over time.

As shown in FIG. 5, the lined cooling element 52 (labeled as Series 1) surprisingly reached an average temperature of 31.46° F. within one minute of being activated (as shown in FIG. 5 at minute 2). The cooling element continues to cool to an average low of 27.14° F. within 4 minutes of activation and remains under 35° F. for at least 30 minutes. By contrast, the control cold packs by Medlogix (FIG. 5, Series 2), even without a lining layer, do not achieve the desired average temperature within a minute of activation. Notably, the Medlogix cold packs, as shown in Series 2, did not reach the desired temperature, but remain at an average of between 45° F. and 50° F.

Figure 6:
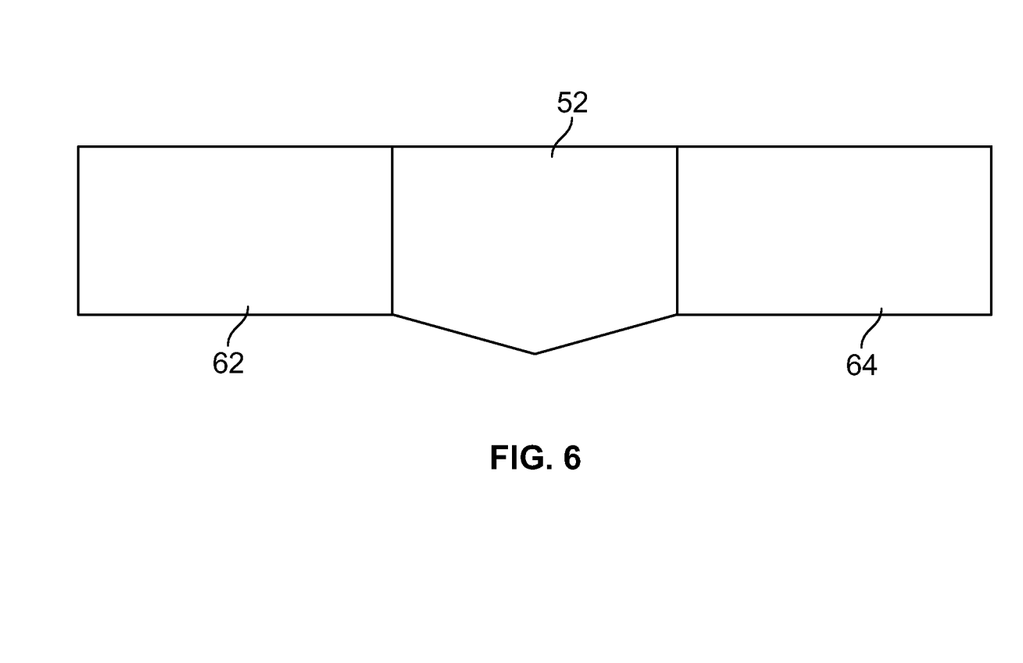
FIG. 6 is a top view of a cooling element for use with a neck band.

The cooling element 52 may also be used without the cooling collar 10 to treat pain or to impart selective brain cooling via the carotid arteries when head and neck injury are not suspected. In this embodiment, shown in FIG. 6, the cooling element may be used in a neck band configuration that comprises a cooling element 52 and a left wing 62 and a right wing 64 attached to each end of the cooling element. The cooling pack 52 may be activated and placed over the patient's carotid arteries, with the wings 62, 64 may be wrapped around the patient's neck and attached to one another in the posterior of the neck with a suitable attachment mechanism, such as a hook and loop fastener (not shown).

In another embodiment, the cooling element 52 may include one or more endothermic packs, such as those containing compartments of ammonium nitrate and water separated by rupturable membranes. In this embodiment, deforming the cooling elements 52 so as to apply differential pressure between the compartments or to otherwise break the membrane can activate such cooling elements 52.

In use, the cervical immobilization collar10 is placed around a patient's neck, and the cooling element 52 is activated and placed in the anterior opening 28. The door 30 is then closed over the cooling element 52, securing the cooling element 52 between the door 30 and the patient's neck. The cooling element 52 will generally overlie the carotid arteries of the patient's neck and function as a heat extractor for withdrawing heat from blood flowing through the patient's carotid arteries. Preferably, the cooling element 52 conforms to the particularities of individual patient's necks, thereby maximizing skin contact area for more efficiently withdrawing heat from neck tissues adjacent to the carotid arteries. In one embodiment, the cooling element 52 conforms to the patient's neck by using pressure members 56 mounted on a body-facing surface of the door 30.

Figure 7:
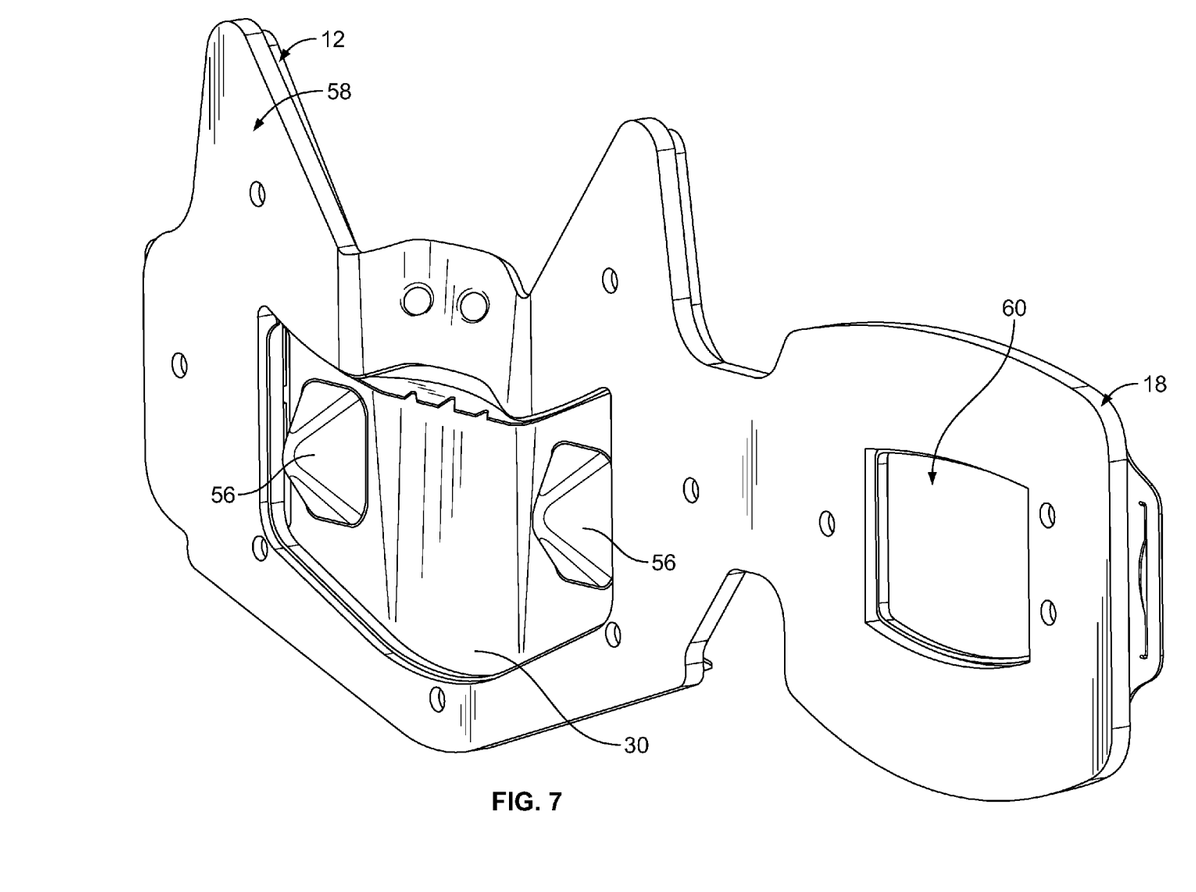
FIG. 7 is a rear view of the cervical immobilization collar.

Specifically, as shown in FIG. 7, the door 30 has a body-facing surface and an outward-facing surface (shown in FIG. 2). As shown, the body-facing surface includes two spaced-apart, pyramid-shaped pressure members 56 that extend toward the user. The pressure members 56 may be formed of other shapes, including blocks, tubes, or any other suitable shape extends toward the patient's neck when the door 30 is closed. The pressure members 56 are placed on the body-facing surface in a position that, when the collar 10 is in use, exerts pressure on the cooling element 52 to maximize skin contact in the carotid artery area. The pressure members 56 may be integrally formed with the body-facing surface of the door 30 or may be attached to the body-facing surface of the door 30 by suitable means, including an adhesive. Alternatively, the pressure member 56 may be integrally formed with the door 30. The pressure members 56 may be made of foam, plastic, or other suitable material. In one embodiment, the pressure members 56 may be made of a 2.8 lb. density open cell urethane foam. The pressure members 56 should be formed so that the pressure exerted on the patient's carotid arties does not block the patient's airway.

As shown in FIG. 7, a foam layer 58 lines the body-facing surface of the substantially annular support structure 12 to provide a better fit with the patient's neck. The foam layer may be formed of an open or closed cell foam, or other suitable material. In this embodiment, the substantially annular support structure 12 and the foam layer 58 include a rear, rectangular opening 60 within posterior portion 18 to provide access to the rear of the patient's neck in case there is a need for additional medical procedures. In an alternative embodiment, there is no opening in the posterior portion 18 of the device.

It is also contemplated that the cervical immobilization collar may incorporate a sensor (not shown) mounted in the vicinity of one of the patient's carotid triangle for monitoring one or more circulatory parameters such as arterial oxygen saturation, heart rate, blood pressure, and blood temperature. For positioning the sensor in direct contact with the patient's skin, a portion of the cooling element may need to be reshaped or displaced. A recording device (not shown) can be located elsewhere inside or outside the collar for recording information collected by the sensors. Other sensors can be mounted elsewhere in the collar for monitoring various body parameters, including body temperature, or for monitoring performance of the immobilization collar itself. For example, a temperature gauge, such as a thermochromic strip, can be used for monitoring the temperature of the collar or the cooling element.

A display (not shown) may be placed on the outside surface of the anterior portion of the same cervical immobilization collar. The display can be used for monitoring the circulatory data collected by the sensor as well as other data collected by other sensors mounted in the collar. A communications port (not shown) can also be formed in the collar for transferring data from the one or more sensors to an external device.

The cervical immobilization collar makes possible a new protocol for treating trauma patients, including patients suffering from head trauma, heart attack, ischemic attack, headache, epilepsy, heat stroke, concussion, or similar conditions. It is envisioned that the protocol may be employed by emergency medical technicians or at hospitals, for home use, by athletic trainers, or the like. The treatment centers on installing a cervical immobilization collar around a patient's neck having facility for limiting rotation and compaction of the patient's cervical vertebrae and using the cooling element with the collar to impart selective cooling of the brain via the carotid arties. The protocol uses vasodilatation of the patient's carotid arties to evoke selective central core brain cooling and mild hypothermia, as opposed to systemic cooling of the body. As opposed to smaller vessels of the body, which respond by constricting when cold is applied to the skin, the larger blood vessels of the body appear to respond by dilating, allowing increased cooled blood to circulate to the brain from the carotid arties The protocol includes determining the size of collar 10 that the patient requires. Available sizes include conventional no neck, short, regular, and tall cervical immobilization collars. The collar 10 is then applied to the patient and the door 30 is opened. The cooling element 52 is then activated by breaking the liquid filled packet and shaking the cooling element 52 for about 15 to about 20 seconds. The cooling element 52 is then placed in the anterior opening 28 in the frame of the substantially annular support structure 12 and secured to the patient's neck by closing the door 30. The cooling element 52 is in thermal transcutaneous communication with at least one of the patient's carotid arteries through an anterior portion of the patient's neck, thus initiating a flow of heat from the one or more carotid arteries through the anterior portion of the patient's neck to the cooling element and the reducing temperature of the patient's brain without inducing systemic hypothermia.

The cooling element 52 should be left in place for approximately 20, but no more than 30 minutes, at which time the first cooling element should be removed and a new cooling element activated and placed within the collar as described above. This protocol may be repeated as needed.

The protocol can also include monitoring one or more parameters related to circulatory performance of the patient through one or more sensors carried by the immobilization collar. The monitored parameters can include oxygen saturation, pulse rate, blood pressure, or blood temperature. Sensors can also be used to monitor the thermal performance of the cooling element. The protocol of claim can also include measuring a pulse rate of the patient manually by temporarily displacing the cooling element from an opening in the collar over the patient's carotid triangle.

Although the invention has been described with respect to a limited number of embodiments, many more variations will be readily apparent to those of skill in the art in accordance with the overall teaching and scope of this invention. For example, the cooling elements could be mounted on both the anterior and posterior portions of the cervical immobilization collar to extract heat from larger portions of the patients' necks. The cooling of both carotid arteries is generally preferred, but the cooling elements could also be fashioned for cooling just one of the carotid arteries, leaving the other carotid artery exposed for other purposes.

The invention claimed is:

1. A cooling element comprising:
 a body-facing panel attached on a body-facing surface;
 an outward-facing panel, wherein the body-facing panel and the outward-facing panel form an end;
 cooling material disposed between the body-facing panel and the outward facing panel, wherein the cooling material is capable of producing a temperature of 20° F. to 35° F. within a minute of activation at ambient temperature, when measured on the body-facing surface of the body-facing panel, and wherein the cooling material comprises water, urea, and an endothermic ingredient; and
 a band attached to the end and configured wrap around a patient.

2. The cooling element of claim 1, wherein the band comprises a wing that extends from the end.

3. The cooling element of claim 2, wherein the wing comprises an attachment mechanism.

4. The cooling element of claim 3, wherein the attachment mechanism is a hook and loop fastener.

5. The cooling element of claim 1, wherein:
 the body-facing panel and the outward-facing panel define an second end;
 the band comprises a first wing that extends from the end, and a second wing that extends from the second end; and
 the first wing and the second wing attach to one another.

6. The cooling element of claim 1, wherein the cooling material comprises a greater amount of the urea than the endothermic ingredient by mass.

7. The cooling element of claim 1, wherein the cooling material comprises at least 45 g of the endothermic ingredient.

8. The cooling element of claim 1, wherein the cooling material comprises at least about 90 g of the urea.

9. The cooling element of claim 1, wherein the cooling material includes 90 to 110 g urea and 45 to 55 g of the endothermic ingredient.

10. The cooling element of claim 1, wherein the cooling material includes 100 g urea and about 50 g of the endothermic ingredient.

11. The cooling element of claim 1, wherein the cooling material includes 110 g urea and about 55 g of the endothermic ingredient.

12. The cooling element of claim 1, wherein the cooling material maintains the temperature for a period of 15 to 30 minutes.

13. The cooling element of claim 1, wherein the body-facing panel is attached on the body-facing surface to a lining layer.

14. The cooling element of claim 13, wherein the lining layer comprises non-woven material.

15. The cooling element of claim 14, wherein the lining layer substantially covers the body-facing surface of the body-facing panel and the outward-facing surface of the outward-facing panel.

16. The cooling element of claim 13, wherein the body-facing panel is attached to the lining layer with an adhesive.

* * * * *